US005132223A

United States Patent [19]
Levine et al.

[11] Patent Number: 5,132,223
[45] Date of Patent: Jul. 21, 1992

[54] PROCESS AND MEDIUM FOR CLONING AND LONG-TERM SERIAL CULTIVATION OF ADULT HUMAN ENDOTHELIAL CELLS

[75] Inventors: Elliot M. Levine, Cherry Hill, N.J.; Sandor S. Shapiro, Philadelphia, Pa.; Bruce E. Jarrell, Philadelphia, Pa.

[73] Assignee: Thomas Jefferson University, Philadelphia, Pa.

[21] Appl. No.: 609,193

[22] Filed: Nov. 5, 1990

Related U.S. Application Data

[60] Division of Ser. No. 210,218, Jun. 17, 1988, Pat. No. 4,994,387, which is a continuation of Ser. No. 99,241, Sep. 21, 1987, abandoned, which is a continuation of Ser. No. 848,913, Apr. 7, 1986, abandoned, and a continuation of Ser. No. 848,917, Apr. 7, 1986, abandoned, which is a continuation of Ser. No. 550,305, Nov. 10, 1983, abandoned, and a continuation of Ser. No. 550,306, Nov. 10, 1983, abandoned.

[51] Int. Cl.$^5$ ............................ C12N 5/08; C12N 5/02
[52] U.S. Cl. ............................ 435/240.2; 435/240.23; 435/240.3
[58] Field of Search ............... 435/240.2, 240.23, 240.3

[56] References Cited

U.S. PATENT DOCUMENTS 4,994,387  2/1991  Levine et al. .................... 435/240.2

OTHER PUBLICATIONS

Glassberg et al., In Vitro 18: 859-866 (1982).
Thornton et al., Science 222: 623-625 (1983).

*Primary Examiner*—Douglas W. Robinson
*Assistant Examiner*—S. Saucier
*Attorney, Agent, or Firm*—Woodcock Washburn Kurtz Mackiewicz & Norris

[57] ABSTRACT

Vigorous growth of endothelial cells from human blood vessels in vitro is achieved using a culture medium containing endothelial cell growth factor and heparin and/or dextran sulfate. Cell population doubling times of 13 to 21 hours for 60 to 85 populations doublings are obtained, and cloned human endothelial cell strains are established having similar proliferative capacities.

11 Claims, 2 Drawing Sheets

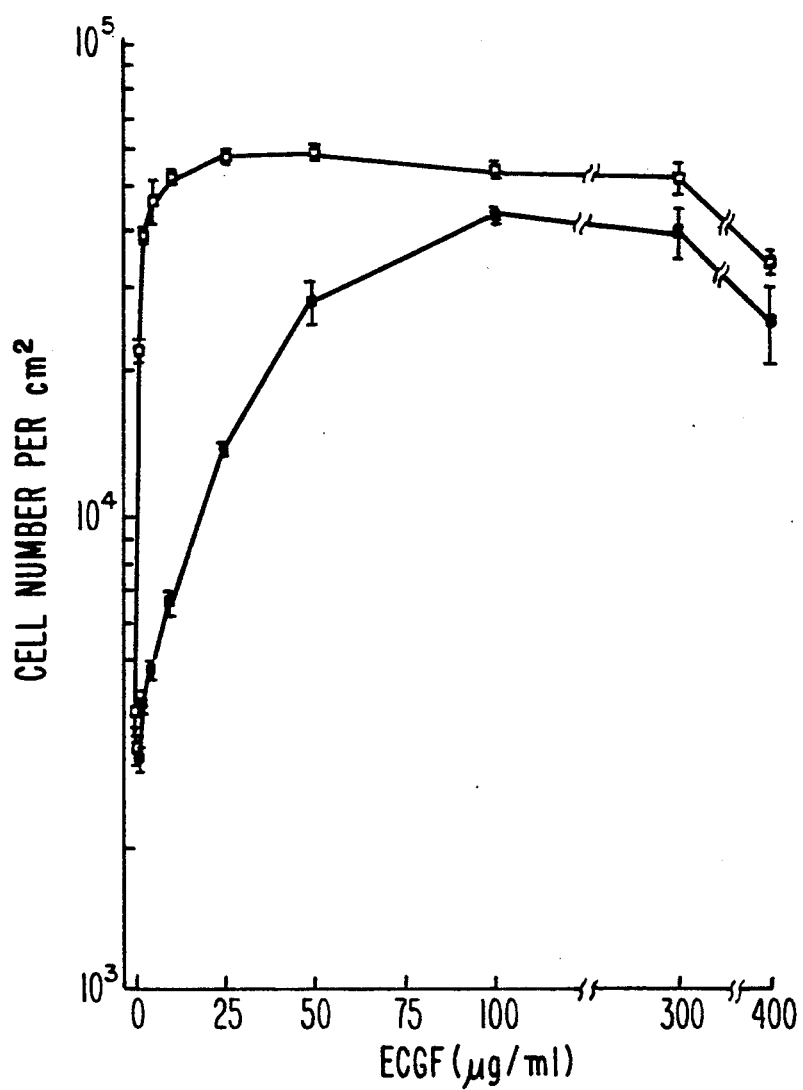
_Fig. 1a_
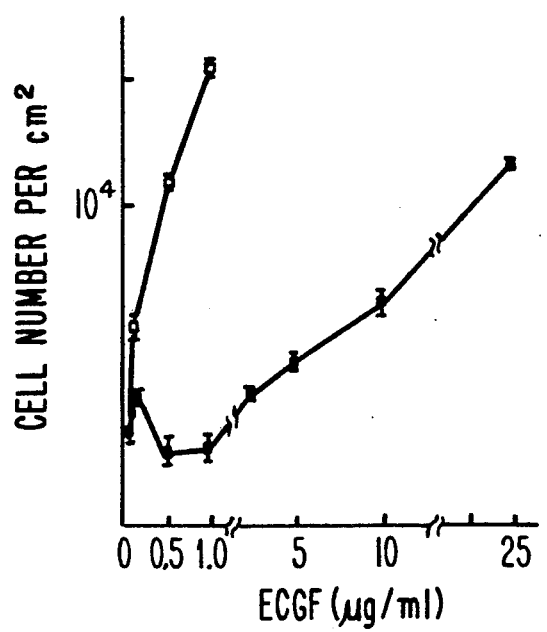
_Fig. 1b_

PROCESS AND MEDIUM FOR CLONING AND LONG-TERM SERIAL CULTIVATION OF ADULT HUMAN ENDOTHELIAL CELLS

This is a division, of application Ser. No. 210,218, filed Jun. 17, 1988 now U.S. Pat. No. 4,994,387, which is a continuation application of Ser. No. 099,241, filed Sep. 21, 1987 (now abandoned), which is a continuation application of Ser. No. 848,913 and 848,917 both filed on Apr. 7, 1986 (now abandoned), which respectively are continuation applications of Ser. No. 550,305 and 550,306, both filed Nov. 10, 1983 (now abandoned).

DESCRIPTION

This invention relates to in vitro cultivation of human endothelial cells, and more particularly to a novel culture medium containing heparin and/or a dextran sulfate, and a process employing such medium for in vitro cultivation of endothelial cells derived from human blood vessels by means of which the proliferative lifespan of such cells is greatly increased.

BACKGROUND OF THE INVENTION

The endothelium forms the luminal surface of the vascular system, and is an integral component in such physiologic functions as wound healing, hemostasis, selective transfer of substances to and from the circulation, and synthesis of numerous metabolically active compounds. Correspondingly, endothelial involvement is prominent in pathologic conditions including atherosclerosis, diabetes, thrombosis, hemorrhagic disorders, tumor metastasis, hypersensitivity, and inflammation (Levine et al *Biochemical Interactions at the Endothelium*, Elsevier, Amsterdam (1983) pp. 313-342). The need for a greater understanding of endothelial function has prompted methodological improvements for culturing this cell in vitro. Bovine endothelial cells have been studied widely due to the ease with which they can be serially subcultivated (Levine et al, supra; Rosen et al, *J. Cell Physiol.* 107, 123 (1981); Mueller et al, *Science* 207, 889 (1980)). Human endothelial cells, however, have more fastidious growth requirements and, despite a suggestion that fibroblast growth factor and thrombin stimulate their growth, (Gospodarowicz et al, *J. Cell Biol.* 77, 774 (1978)), little progress has been made in the long-term serial subcultivation of these cells (Maciag et al, *J. Cell Biol.* 91, 420 (1981); Glassberg et al, *In Vitro* 18, 859 (1982); (Johnson, *J. Clin. Invest* 64, 841 (1980); Gimbrone, Jr., et al, *J. Cell Biol* 60, 673 (1974); Jaffe et al, *J. Clin. Invest.* 52, 2745 (1973); Haudenschild et al, *J. Ultrastruct. Res.* 50, 22 (1975); Gordon et al, *J. Cell Biol.* 91, 205A (1981)).

A significant advance in this field was the use of endothelial cell growth factor (ECGF) and fibronectin to enhance the replicative capacity of human umbilical vein endothelial (HUVE) cells (Maciag et al., supra). These factors allowed HUVE cells to be subcultivated; however, multiplication was slow (2-3 day doubling time) and short lifespan (27-34 population doublings (PDs)). Human endothelial cells isolated from adult iliac artery and grown under the same conditions exhibited an even shorter lifespan (15-18 PDs) (Glassberg et al, supra). In no case have cloned strains of human endothelial cells been reported.

BRIEF SUMMARY OF THE INVENTION

This invention is predicated on the discovery that heparin and/or a dextran sulfate greatly potentiate the stimulatory effect of endothelial cell growth factor on the proliferation of human umbilical vein endothelial cells and of endothelial cells from adult human blood vessels. It was discovered that by growing cells on a gelatin matrix in a culture medium supplemented by both endothelial cell growth factor and heparin and/or a dextran sulfate, it was possible to subcultivate and clone human endothelial cells from various blood vessels on the order of from about 60 to 85 population doublings (PDs) with doubling times of 13 to 21 hours.

BRIEF DESCRIPTION OF THE FIGURES

FIG. 1 comprises graphs in which endothelial cell number per $cm^2$ is plotted against concentration of endothelial cell growth factor in a culture medium containing 90 $\mu g/ml$ of heparin (open circles) and another containing no heparin (solid dots). The graphs of the insert in FIG. 1 are based on the same data as the larger graphs, but replotted on an expanded scale for ECGF concentrations between 0 and 25 $\mu g/ml$.

DETAILED DESCRIPTION OF THE INVENTION

Figure 2:
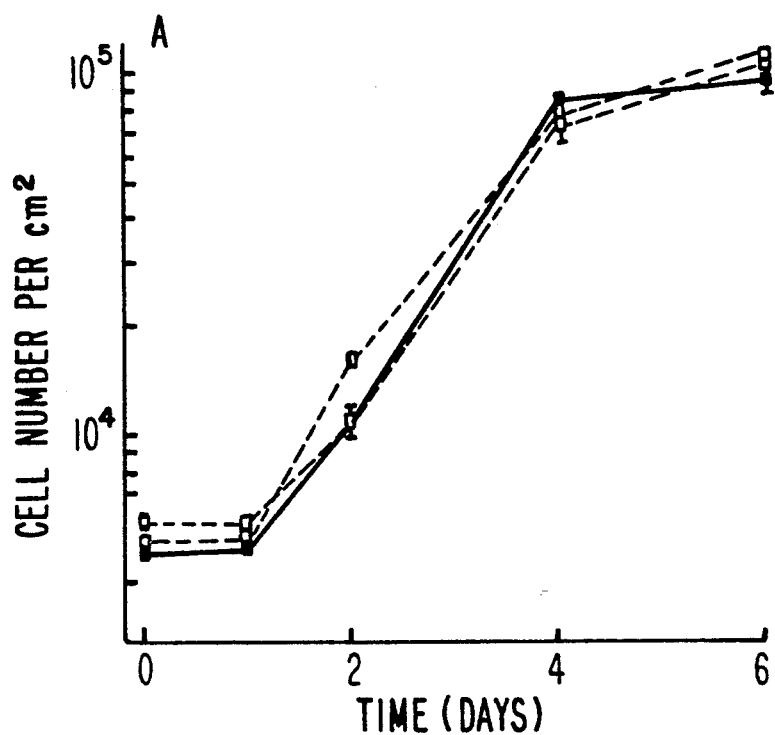
FIG. 2 comprises three curves of growth (cell number /$cm^2$) versus time for three different human umbilical vein endothelial cell lines indicated by open squares, solid squares and open circles, respectively.

As noted above, HUVE cells have been subcultured in culture medium containing endothelial cell growth factor (Maciag et al, supra), but multiplication was slow (2-3 days doubling time) and short lifespan (27-34 population doublings). Even a shorter life span (15-18 PDs) was observed for human endothelial cells from adult iliac artery. It was discovered, however, that if heparin and/or a dextran sulfate are included in the culture medium, doubling times were substantially reduced to 13 to 21 hours, and 60 to 85 population doublings are obtained before senescence.

The endothelial cell culture medium used in the process of this invention comprises any of the well known media for culturing cells, fetal bovine serum, endothelial cell growth factor and heparin and/or dextran sulfate. Of the various cell growth media, Medium 199 (Gibco Laboratories) is particularly preferred. The composition of such medium is well known (see e.g. Morgan et al, *Proc. Soc. Biol. Med*, 73, 1 (1950)).

In addition to the cell culture medium, such as Medium 199, the endothelial cell culture medium of the invention contains endothetial cell growth factor which is available from Collaborative Research, Inc. ECGF may be prepared as described by Maciag et al, supra. The mode of preparation therein described involves preparing hypothalamic extracts by homogenization of bovine hypothalamus followed by stirring of the homogenate for a period of hours at 4° C., centrifugation and recovery of the supernatant. The resulting extract is then further fractionated with streptomycin sulfate (Gibco) to remove soluble lipid. The supernatant is extracted with 0.5% streptomycin sulfate at pH 7.0 for at least 1 hour, after which the extract is centrifuged at 13,800× g for 40 minutes and the supernatant is recovered and can be stored as a lyophilized powder at 4° C. The resulting ECGF is an acid-and heat-labile protein, physically and chemically distinct from fibroblast growth factor (Gospodarowicz et al, *J. Biol. Chem.* 253, 3736–3743 (1978)), possessing a molecular weight of 75,000 (Maciag et al, *Proc. Natl. Acad. Sci. U.S.A.*, 76, 5674–5678 (1979)).

Heparin has a molecular weight of 6000–25,000 and is a glycosaminoglucuronan (acid mucopolysaccharide) that occurs in most tissues; human liver, lung and mast cells are especially rich sources. Chemically it is not homogeneous, but is a family of linear polymers which differ in chain length and M.W., but have similar disaccharide units. The disaccharide units are composed of D-glucuronic or L-iduronic acids in 1,4-glycosidic linkage to glucosamine; each unit contains two sulfate esters and one N-sulfate group.

Heparin is obtained commercially from a variety of animal tissues, particularly bovine lung tissue and intestinal mucosa of pigs (see Kirk-Othmer, *Encycl. Chem. Tech.* 3d 4, pp 14–15 (1978)).

Dextran sulfate is usually available as the sodium salt, and chemically is known as dextran sulfuric acid ester sodium salt. It is prepared by boiling dextran with sulfuric acid to reduce the molecular weight and esterifying the degraded dextran with chlorosulfonic acid in pyridine. The molecular weight may vary from about 5000 to about 600,000, and the dextran may contain up to about 25%, by weight, of sulfur. It is a white powder, soluble in water and has an activity of about 17 international heparin units/mg (see e.g. *The Merck Index* 9d (1976) page 2911). The preferred dextran sulfates for use in the endothelial cell culture media of the present invention are one having a molecular weight of about 8000, and another having a molecular weight of about 500,000.

The endothelial cell culture medium of this invention will comprise in addition to a standard cell culture medium, such as Medium 199, from about 5 to about 30%, preferably about 20%, by volume of fetal bovine serum, said percentages being based on the total volume of the endothelial cell culture medium. In addition, such novel culture medium will contain from about 10 to about 200 µg/ml of endothelial cell growth factor and from about 9 to about 900 µg/ml of heparin, or about 5 to about 500 µg/ml of dextran sulfate of MW about 8000, or about 50 to about 500 µg of a dextran sulfate having a MW of about 500,000. Mixtures of heparin and dextran sulfate may also be used. Preferably, the novel endothelial cell culture medium contains on the order of about 20 µg/ml of ECGF and about 90 µg of heparin, or 100 µg of dextran sulfate.

In carrying out the process of this invention, the endothelial cells are isolated and seeded into gelatin-coated flasks containing the above-described endothelial cell culture medium. At confluence, the cells are trypsinized and reseeded at desired cell densities. Clones are derived from secondary cultures and seeded at about 10 cells/cm². The clones are then serially propagated in the said endothelial cell culture medium.

The below described specific examples, figures and tables further serve to illustrate the invention.

In the case where the endothelial cells are to be obtained from human vascular tissue, they preferably are obtained from brain-dead but heart-beating cadaver organ, e.g. kidney donors. Under sterile conditions the abdomen of the heart-beating cadaver donor is entered and the aorta, inferior vena cava (IVC), kidneys and ureters are dissected out "en bloc." At completion of the dissection, but prior to separation of the organs from the circulatory system and removal, the donor is given from at least about 10,000 to 20,000 units, preferably about 15,000 units intravenous aqueous heparin and from at least about 5 to about 15 mg, preferably about 10 mg phenoxybenzamine. The vessels are transected and the kidneys rapidly cooled with iced saline for preservation for future transplant. All tissue is then dissected from the renal vessels, leaving renal artery and vein and a small patch of aorta and inferior vena cava. The remaining tissue of the aorta, IVC and iliac vessels, previously discarded in the course of donor nephrectomy, is placed in labelled specimen containers on ice containing the endothelial cell culture medium of this invention, previously described. The amount of each vessel which can routinely be retrieved at this stage is as follows:

| Vessel | Diameter (cm) | Length (cm) |
| --- | --- | --- |
| Aorta | 1.5–2.5 | 4–6 |
| IVC | 2–3 | 6–8 |
| Left iliac artery | 0.8–1.5 | 4–6 |
| Right iliac artery | 0.8–1.5 | 4–6 |
| Left iliac vein | 1–2 | 4–6 |
| Right iliac vein | 1–2 | 4–6 |

The time elapsed from heparinization until the specimens are placed in containers usually does not exceed about 30 minutes, and tissue perfusion usually continues for most or all of that time. The vascular specimens thus obtained are stored in a cold room. Inasmuch as the surgery is usually performed at night, the specimens are available for use the morning following surgery.

Endothelial cells were isolated from a variety of human blood vessels using collagenase (Rosen, et al, supra), and seeded into gelatin (1%)-coated flasks containing Medium 199 (Gibco Laboratories) with 20% fetal bovine serum, 20 µg/ml ECGF, and 90 µg/ml heparin. At confluence, cultures were tryspinized (0.25% trypsin-0.09% EDTA) and reseeded at desired cell densities. In addition to the umbilical vein, the donor vessels include the superior mesenteric, iliac, carotid, pulmonary, femoral, and splenic arteries, the thoracic and abdominal aortas, and the iliac and portal veins. Clones were derived from secondary cultures by seeding at 10 cells/cm² and isolating single cells with glass cloning rings; approximately half the isolated cells grew and were serially propagated in the above described medium containing ECGF and heparin. Eleven cloned HUVE cell strains and four abdominal aorta endothelial cell strains were established. All cultures were characterized as endothelial according to morphological and functional criteria (expression of Factor VIII-related antigen (Rosen, et al, supra) and production of angiotensin-converting enzyme (Levine et al, supra; Ryan et al *Biochem J.*, 167, 501 (1977)).

Enhanced proliferation and increased lifespan of the human endothelial cell cultures resulted from the inclusion of heparin to the culture medium. Referring to FIG. 1, there is shown the effect of heparin on HUVE cell growth as a function of ECGF concentration. In the presence of heparin significant growth was observed with as little as 1 µg/ml ECGF with maximal growth at 25 µg/ml ECGF; in the absence of heparin, 100–200 µg ECGF were required for significant growth. Cultures supplemented with heparin grew to consistently higher densities than those without heparin. Heparin at concentrations as high as 900 μg/ml did not support replication in the absence of ECGF, demonstrating that both factors were required for optimum growth.

FIG. 2 shows growth curves for three lines of HUVE cells cultured with 90 μg/ml herparin and 20 μg/ml ECGF; these cultures achieved cell densities at confluence of $10^5$ cells/cm$^2$ with doubling times of 17-21 hours. In contrast, cells cultured with 100 μg/ml ECGF without heparin were reported to grow to maximum densities of $4 \times 10^4$ cells/cm$^2$ with a doubling time of 64 hours (Maciag et al, supra).

Figure 3:
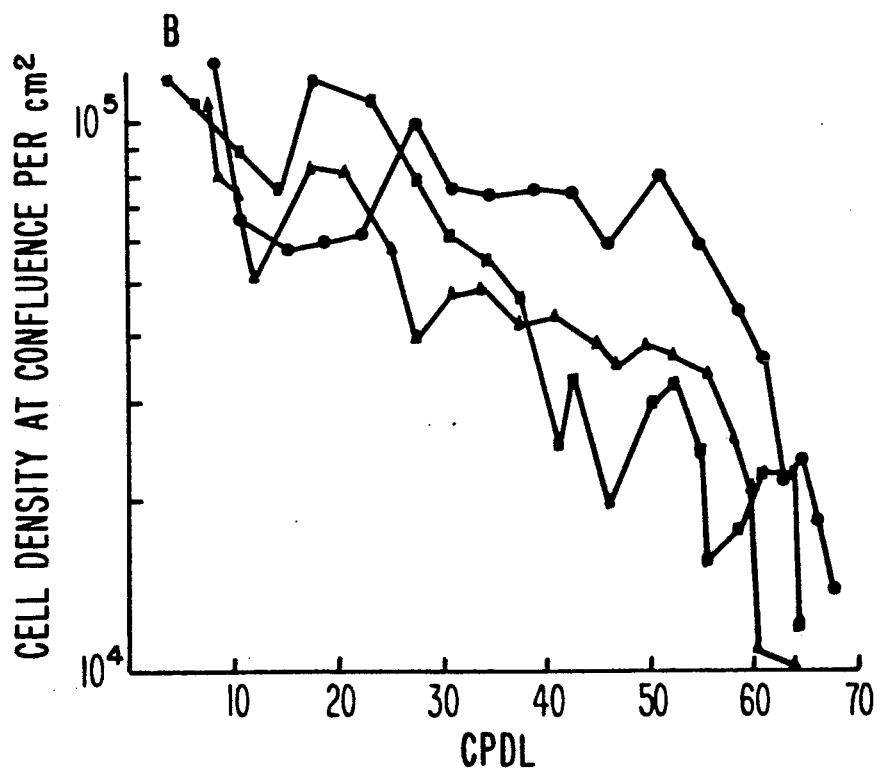
FIG. 3 is a plot of cell density at subculture versus cumulative population doubling level for three separate HUVE cell lines indicated by solid squares, triangles and dots, respectively, subcultured weekly.

FIG. 3 shows cell densities at confluence throughout the lifespan of HUVE cells. Proliferative lifespan was determined by measuring harvest cell density at each subculture until proliferation ceased (Rosen et al, supra). The PDs undergone at each subculture were calculated using the formula: PDs=log$_2$ [(number of cells harvested)/(number of cells seeded)×(attachment efficency)], and summed to give the cumulative population doubling level (CPDL). In all three lines harvest cell densities decreased with increasing CPDL as greater numbers of large nondividing cells appeared. Cultures were considered senescent when less than one PD occurred within three weeks after subculture.

By this definition, the lifespan of 12 uncloned lines and 11 cloned strains of HUVE cells ranged from 42 to 85 with a median of 65 CPDLs. Endothelial cells from adult human vascular tissue exhibited shorter doubling times, and maintained higher harvest cell densities for a greater percentage of their lifespan than HUVE cells. As can be seen by reference to Table 1, lifespan of the cells, in terms of population doublings range from 45 to 66.

TABLE 1

| Culture Designation | Cell Type of Origin | Age of Donor | Sex of Donor | Cause of Death | Lifespan (population doublings) |
|---|---|---|---|---|---|
| Summary of Adult Human Endothelial Cell Lines | | | | | |
| HAAE-1 | Abdominal aorta | 20 | M | Head trauma | 64 |
| Clones | | | | | |
| HAAE-1B | | | | | 45 |
| HAAE-1E | | | | | 62 |
| HAAE-1C | | | | | 78 |
| HAAE-1F | | | | | 67 |
| HAAE-2 | Abdominal aorta | 51 | M | Brain abcess | 61 |
| HIVE-2 | Iliac vein | 51 | M | Brain abcess | 56 |
| HFAE-2 | Femoral artery | 51 | M | Brain abcess | 66 |
| HPAE-2 | Pulmonary artery | 51 | M | Brain abcess | N.D.* |
| HPtVE-2 | Portal vein | 51 | M | Brain abcess | N.D. |
| HMAE-2 | Superior mesentric artery | 51 | M | Brain abcess | N.D. |
| HIAE-3 | Iliac artery | 32 | M | Head trauma | |
| Summary of Adult Human Smooth Muscle Cell Lines | | | | | |
| HTAS-2 | Thoracic aorta | 51 | M | Brain abcess | N.D. |
| HCAS-2 | Carotid artery | 51 | M | Brain abcess | N.D. |
| HAAS-1 | Abdominal aorta | 20 | M | Head trauma | |

*Not determined, frozen at early passage

To confirm that heparin is responsible for stimulating proliferation, the effect of the heparin antagonist, protamine, was examined, and the results obtained are set forth in Table 2, below.

TABLE 2

Effect of Protamine on Human Endothelial Cell Growth

| Additions to Culture Medium$^a$ (μg/ml) | | | Harvest Cell Density$^b$ ($\times 10^4$ cells/cm$^2$) |
|---|---|---|---|
| ECFG | Heparin | Protamine | |
| 20 | — | — | 1.4 + 0.1 |
| 20 | 90$^c$ | — | 5.8 + 0.3 |
| 20 | 90 | 230 | 1.1 + 0.3 |
| 20 | 900 | 230 | 6.2 + 0.2 |
| 200 | — | — | 5.4 + 0.4 |
| 200 | — | 1200 | 0.7 + 0.01 |
| 200 | 990 | 1200 | 9.7 + 0.01 |

$^a$ECGF prepared as described previously (Maciag et al, supra) heparin (sodium salt, Grade 1, from porcine intestine mucosa; 168 U/mg; Sigma); protamine sulfate (sodium salt, Grade X, from salmon sperm; Sigma; 150 μg protamine neutralized 100 μg heparin).
$^b$Cell counts [+ standard deviation, (n = 3)] seven days after seeding at 5 × 10$^3$ cells/cm$^2$.
$^c$Heparin from bovine lung (sodium salt, U.S.P.; Upjohn).

As shown in Table 2, stimulation of cell growth by heparin was completely blocked by a neutralizing dose of protamine. Growth promoting activity was reestablished by addition of a tenfold excess of heparin. At high ECGF concentrations (200 μg/ml) significant growth stimulation was observation in the absence of added heparin. The stimulatory activity of 200 μg/ml ECGF was completely blocked by addition of a high dose of protamine (1200 μg/ml); stimualation of cell proliferation was restored by addition of excess heparin (990 μg/ml). In addition to heparin, the glycosaminoglycans, chondroiton surface, hyaluronic acid and keratin sulfate, were tested for growth promoting capabilities and had no effect on endothelial cell growth. The sulphated polyasccharide, dextran sulphate, significantly stimulated proliferation, although dextran itself was inactive.

The mechanism by which heparin stimulates human endothelial cell proliferation is unknown. Azizkhan et al, J. Exp. Med. 152, 931 (1980) showed that heparin (and dextran sulfate) increased bovine capillary endothelial cell migration, but had no effect on proliferation. Other reports on the effects of heparin on various cell types have yielded conflicting results (Costachel et al, Exp. Cell Res. 34, 542 (1964); Young et al, Proc. Soc. Exp. Biol. Med 159, 88 (1978); Castellot, Jr. et al, J. Cell Biol. 90, 372 (1981); Lippman, Epithelial-Mesenchymal Interactions, 18th Hahnemann Symposium (Williams and Wilkins, Baltimore 1968) pp. 208-229). Several investigations have shown that heparin may bind reversibly or irreversibly to the cell surface (Lippman, supra; Kjellén et al, Biochem. Biophys. Res Comm 74, 126 (1977); Glimelius et al, Thromb. Res. 12, 773 (1978)) and, thus, may influence intercellular communication (Roblin et al, Biochemistry 14, 347 (1975); Ohnishi, et al, Exp. Cell Res. 93, 136 (1975)) and membrane receptor accessibility (Kraemer et al, Biochem. Biophys. Res. Comm. 56 423 (1974)). Morphologic changes (Abro et al, Experimentia 31 1453 (1975)) and modifications of cellular behavior (Azizkhan et al, supra; Regelson, Advances in Chemotherapy, Academic Press, New York (1968) Vol. 3, pp 303-370) consistent with cell membrane-heparin interactions have been reported. In vivo, the extracellular matrix of vascular tissue contains high concentrations of glycosaminoglycans (Gardais et al, Comp. Biochem. Physiol. 44B 507 (1973)). In vitro, heparin-like molecules are secreted by endothelial cells (Buonassisi, Exp. Cell Res. 76, 363 (1973); Busch, et al,

*Haemostasis* 8, 142 (1979); Gamse et al, *Biochem Biophys. Acta* 544, 514 (1978)) and have been shown to inhibit smooth muscle cell growth (Castellot et al, supra). The discovery that heparin stimulates endothelial cell proliferation suggests that heparin-like substances may play an important role in cell growth regulation in normal and injured vessels.

In the past, many basic and applied studies had to be performed on endothelial cells from other animal species because existing culture techniques permitted only restricted proliferation of human endothelial cells. It is believed that the procedures of this invention described above for serial subcultivation can increase the yield of HUVE cells by $10^8$-fold and of adult vessel endothelial cells by $10^{13}$-fold over previously published methods. This will permit minimal amounts of human vascular tissue to be used for the generation of large numbers of cultured endothelial cells, and thus, problems of human pathology involving the endothelium now can be approached directly employing a human endothelial cell model. In addition, this cell system should prove valuable for various clinical applications, such as in vitro testing of vasoactive agents and the coating of artificial graft materials.

We claim:

1. A process for enhancing proliferation and increasing the lifespan of adult vessel human endothelial cell cultures which comprises culturing adult vessel human endothelial cells in the presence of a cell culture medium containing effective amounts of endothelial cell growth factor (ECGF) and a material selected from the group consisting of heparin, dextran sulfate, and mixtures thereof.

2. The process of claim 1 in which said endothelial cell culture medium comprises from about 5 to about 30% fetal bovine serum and from about 70 to about 95% of a cell culture medium, said percentages being by volume based on the total volume of said endothelial cell culture medium.

3. The process according to claim 2 in which said culture medium contains from about 10 to about 200 µg/ml of endothelial cell growth factor and from about 9 to about 900 µg/ml of heparin.

4. The process of claim 3 in which said culture medium comprises about 20% fetal bovine serum and contains about 20 µg/ml of endothelial cell growth factor and about 90 µg/ml heparin.

5. The process of claim 2 in which said culture medium contains from about 10 to about 200 µg/ml of endothelial cell growth factor and from about 5 to about 500 µg/ml of dextran sulfate.

6. the process of claim 5 in which said culture medium comprises about 20% fetal calf serum, and contains about 100 µg/ml of dextran sulfate.

7. The process of claim 1 in which said cell culture is trypsinized when a cell density of at least about $6 \times 10^4/cm^2$ is obtained, subcultures are reseeded at predetermined densities from said trypsinized cultures, clones are derived from said secondary cultures, and said clones are serially propagated in said cell culture medium.

8. The process of claim 1 in which said endothelial cells are derived from adult human vascular tissue obtained from a brain-dead, heart-beating cadaver donor.

9. The process according to claim 8 in which said cadaver donor is given from about 10,000 to about 20,000 units intravenous aqueous heparin and from about 5 to about 15 mg of phenoxybenzamine prior to dissection and removal of said vascular tissue from said cadaver.

10. The process according to claim 9 in which said cadaver donor is given about 15,000 units intavenous aqueous heparin and about 10 mg phenoxybenzamine prior to dissection and removal of said vascular tissue from said cadaver.

11. The process according to claim 8 in which said vascular tissue is placed immediately after being obtained in an endothelial growth medium comprising about 20% fetal bovine serum, about 80% cell culture medium and containing about 20 µg/ml of endothelial cell growth factor and about 90 µg/ml heparin.

* * * * *